United States Patent
Heckele et al.

(10) Patent No.: US 6,565,587 B1
(45) Date of Patent: May 20, 2003

(54) CUTTER FOR REMOVING TISSUE

(75) Inventors: Helmut Heckele, Knittlingen (DE); Eberhard Körner, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/901,179

(22) Filed: Jul. 9, 2001

(30) Foreign Application Priority Data

Aug. 7, 2000 (DE) .......................................... 100 38 480

(51) Int. Cl.⁷ ............................................ A61B 17/32
(52) U.S. Cl. ................................................... 606/167
(58) Field of Search ................. 606/167, 170, 606/80; 604/22

(56) References Cited

U.S. PATENT DOCUMENTS

| | | | | |
|---|---|---|---|---|
| 4,951,690 A | * | 8/1990 | Baker .......................... 128/898 |
| 5,409,454 A | * | 4/1995 | Fischell et al. ................ 604/22 |
| 5,569,254 A | * | 10/1996 | Carlson et al. ............... 600/101 |
| 5,591,170 A | * | 1/1997 | Spievack et al. .............. 30/122 |
| 5,643,298 A | * | 7/1997 | Nordgren et al. .............. 604/22 |
| 5,833,704 A | * | 11/1998 | McCombs et al. ............ 408/226 |
| 5,913,867 A | * | 6/1999 | Dion ........................... 606/170 |
| 6,033,409 A | * | 3/2000 | Allotta ........................ 606/170 |
| 6,206,898 B1 | * | 3/2001 | Honeycutt et al. ........... 606/159 |
| 6,287,114 B1 | * | 9/2001 | Meller et al. ................ 433/165 |

FOREIGN PATENT DOCUMENTS

| | | |
|---|---|---|
| DE | 38 40 466 A1 | 6/1990 |
| DE | 38 08 410 C2 | 7/1993 |
| FR | 2 044 535 | 2/1971 |
| WO | WO 93/09731 A1 | 5/1993 |

* cited by examiner

*Primary Examiner*—Kevin T. Truong
*Assistant Examiner*—Victor Nguyen
(74) *Attorney, Agent, or Firm*—Akin Gump Strauss Hauer & Feld, L.L.P.

(57) ABSTRACT

A cutter for removing tissue has a cutter head, a cutter shank which carries the cutter head and to which the cutter head is connected in a rotationally fixed manner, and a drive driving the cutter shank. For adjustability of the effectiveness of the cutter with the removal of cartilaginous or bony tissue parts, there is provided a first rotatable sleeve which comprises an inner bore arranged eccentrically to the middle axis of this sleeve, and a second stationary sleeve arranged in the inner bore of the first sleeve and which for passage of the cutter shank comprises an inner bore arranged eccentrically to the middle axis of the second sleeve.

10 Claims, 2 Drawing Sheets

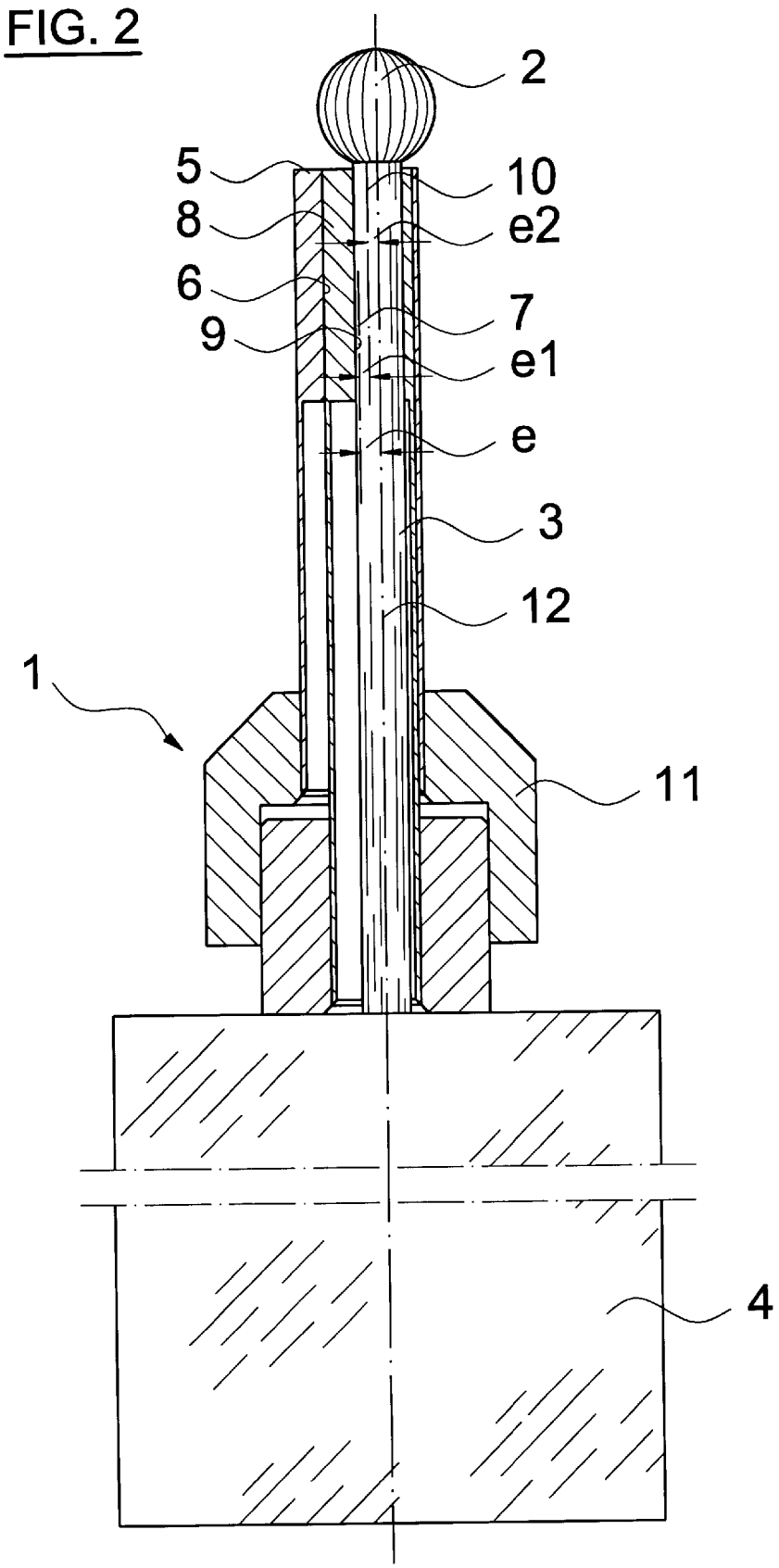

CUTTER FOR REMOVING TISSUE

BACKGROUND OF THE INVENTION

The invention relates to a cutter for removing tissue, with a cutter head, with a cutter shank which carries the cutter head and to which the cutter head is connected in a rotationally fixed manner, and with a drive driving the cutter shank.

Cutters of the previously known type are known in surgery. They are used in order to remove bony or cartilaginous tissue. The cutter head therein may be arranged eccentric to the cutter shank. It is consequently achieved that the cutter head with each revolution projects radially outwards over a defined angular path beyond a stationary sleeve or a stationary shank and may remove tissue.

With such cutters there arises, however, an unbalanced mass which is not insignificant and which impedes the machining accuracy. Furthermore, the effective active regions of the cutter are very difficult to determine accurately so that, inasmuch as this is concerned, the accuracy of the tissue removal is limited.

BRIEF SUMMARY OF THE INVENTION

It is therefore the object of the invention to develop further a cutter of the initially mentioned type, such that the safety and the accuracy with its use is increased and the tissue removal may be effected with an increased precision. Furthermore, the efficiency of the removal is to be increased and the working range—exactly adjustable—is to be increased.

For achieving this object the cutter according to the invention is characterized by a first rotatable sleeve which comprises an inner bore which is arranged eccentrically to the middle axis of this sleeve, and by a second stationary sleeve which is arranged in the inner bore of the first sleeve and which for the passage of the cutter shank comprises an inner bore which is arranged eccentrically to the middle axis of the second sleeve.

The arrangement of two sleeves, each with an eccentric bore, for the radial mounting of the cutter shank is achieved in a simple manner in that, by rotation of the two sleeves relative to one another, the cutter head with respect to its radial projection beyond the outer circumference of the outer sleeve may be adjusted simply and continuously in an exact manner. The effective effect of the cutter head with the removal of tissue may thus be exactly adjusted.

The handling of the cutter is simplified in that the second sleeve is connected to the drive or its housing in a rotationally fixed manner. Furthermore, the first sleeve is preferably connected in a rotationally fixed manner to a rotatable handle. With the latter, the effective eccentricity of the cutter head may be simply adjusted.

Furthermore, the eccentricity of the inner bore of the first sleeve and the eccentricity of the inner bore of the second sleeve are equally large. It is consequently achieved that, by way of a suitable rotation of the two sleeves relative to one another or of the first sleeve relative to the second stationary sleeve, the eccentric projection of the cutter head may be adjusted from zero up to a maximum value.

Preferably, the second sleeve with its outer diameter is arranged in the inner bore of the first sleeve with a clearance fit. Furthermore, between the outer diameter of the second sleeve and the inner bore of the first sleeve there may be arranged a sliding bearing, or this region may be designed as a sliding bearing.

With regard to manufacturing and assembly technology, there results a simple embodiment when the cutter head and the cutter shank are formed as one piece. Furthermore, the cutter shank may be connected to the drive shaft by way of a positive-fit connection. Finally, the cutter shank may be connected to the drive shaft further by way of a snap connection.

For reducing the weight of the cutter, the first and/or the second sleeve is essentially designed as a solid component only in the region neighboring the cutter head, and in the region neighboring the drive as a hollow component.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment, which is presently preferred. It should be understood, however, that the invention is not limited to the precise arrangements and instrumentalities shown. In the drawings:

FIG. 2 is a side view, partially in section, of a cutter of the invention with an adjusted maximal eccentricity of the cutter head with respect to the outer sleeve.

DETAILED DESCRIPTION OF THE INVENTION

Figure 1:
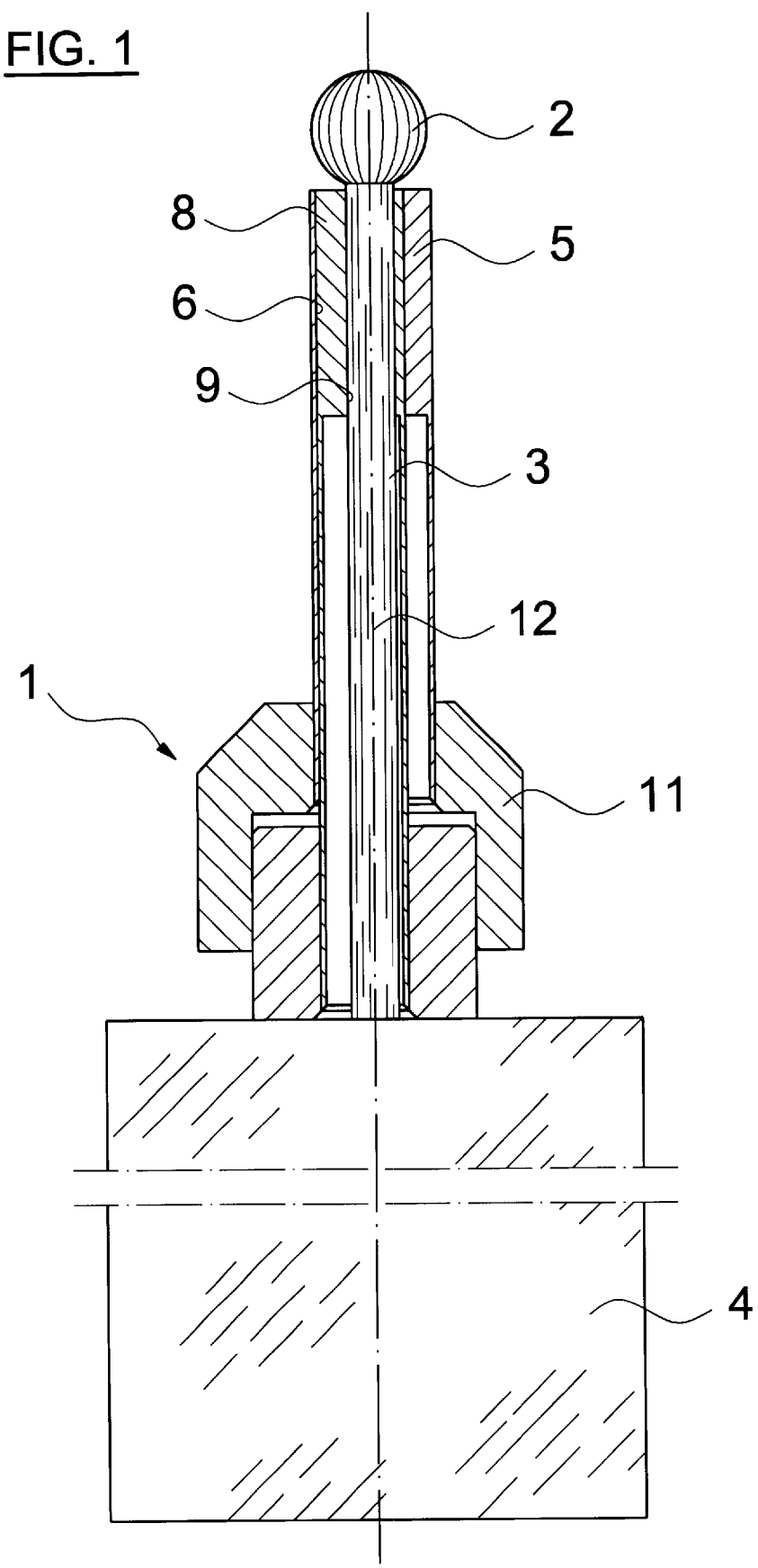
FIG. 1 is a side view, partially in section, of a cutter of the invention without an adjusted eccentricity.

In FIG. 1 there may be seen a cutter 1 which comprises a drive 4, which via a cutter shank 3 drives the cutter head 2. The cutter shank 3 is guided in a system of two sleeves 5 and 8. The first sleeve 5 herein comprises an inner bore 6, in which the second sleeve 8 is accommodated. The second sleeve 8 has, in turn, an inner bore 9, which serves for the passage and the mounting of the cutter shank 3.

The first sleeve 5 and the second sleeve 8 carry their respective inner bores 6 and 9 eccentrically, that is to say the bore axes are not identical to the central axes 7 and 10 of the sleeves 5 and 8, respectively. In FIG. 2 it is to be recognized that the inner bore 6 is incorporated in the inner sleeve 5 with the eccentricity $e_1$, while the second sleeve 8 carries its inner bore 9 with the eccentricity $e_2$.

In the position of the two sleeves 5 and 8 relative to one another, represented in FIG. 2, there thus results as a total eccentricity of the axis of the cutter head 2 or cutter shank 3 with respect to the middle axis 7 of the first sleeve 5 a value of $e = e_1 + e_2$.

In contrast, in FIG. 1 the first sleeve 5 is rotated or adjusted relative to the second sleeve, such that there results no eccentricity of the cutter head 2 relative to the middle axis 7 of the first sleeve 7. This is achieved in that both eccentricities $e_1$, $e_2$ are equally large, the sleeves 5 and 8 however are rotated relative to one another such that both eccentricities are lifted and the middle axis of the cutter shank 3 is identical to the middle axis 7 of the first sleeve 5. Thus, there results no eccentric running of the cutter head 2 relative to the first sleeve 5.

By rotating the handle 11 which is connected to the first sleeve 5 in a rotationally fixed manner, then there may be infinitely adjusted an eccentricity between zero and e, by which means the cutter 1 may be adapted to the respective working conditions.

The cutter 1 is preferably suitable for removing cartilaginous or bony tissue in the region of the vertebral column.

This is particularly the case for the endoscopic application of the cutter. An especially exact removal is thereby achieved in this case. The cutter runs with a balanced mass, and the adjusting of the necessary working eccentricity or working depth may be effected infinitely, exactly and in a simple manner.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A cutter for removing tissue, comprising a cutter head, a cutter shank carrying the cutter head and to which the cutter head is connected in a rotationally fixed manner, a drive for the cutter shank, a first rotatable sleeve having an inner bore arranged eccentrically ($e_1$) to a central axis of the first sleeve, and a second stationary sleeve arranged in the inner bore of the first sleeve and having an inner bore for passage of the cutter shank arranged eccentrically ($e_2$) to a central axis of the second sleeve.

2. The cutter according to claim 1, wherein the second sleeve is connected to a housing of the drive in a rotationally fixed manner.

3. The cutter according to claim 1, wherein the first sleeve is rigidly connected to a rotatable handle.

4. The cutter according to claim 1, wherein the eccentricity $e_1$ of the inner bore of the first sleeve and the eccentricity $e_2$ of the inner bore of the second sleeve are equally large.

5. The cutter according to claim 1, wherein the second sleeve has its outer diameter arranged with a clearance fit in the inner bore of the first sleeve.

6. The cutter according to claim 5, wherein between the outer diameter of the second sleeve and the inner bore of the first sleeve there is provided a sliding bearing.

7. The cutter according to claim 1, wherein the cutter head and the cutter shank are formed as one piece.

8. The cutter according to claim 1, wherein the cutter shank is connected to a shaft of the drive by a positive-fit connection.

9. The cutter according to claim 1, wherein the cutter shank is connected to a shaft of the drive by a snap connection.

10. The cutter according to claim 1, wherein the first sleeve and the second sleeve are formed essentially as a solid component only in a region neighboring the cutter head and in a region neighboring the drive as a hollow component.

* * * * *